US012036184B2

(12) United States Patent
Bokvist et al.

(10) Patent No.: US 12,036,184 B2
(45) Date of Patent: Jul. 16, 2024

(54) PACIFIER WITH FLUID PASSAGEWAY AND EXCHANGEABLE HOUSING

(71) Applicant: VIVOLAB AB, Falun (SE)

(72) Inventors: Fredrik Bokvist, Svardsjo (SE); Lars Thelin, Falun (SE)

(73) Assignee: VIVOLAB AB, Falun (SE)

( * ) Notice: Subject to any disclaimer, the term of this patent is extended or adjusted under 35 U.S.C. 154(b) by 519 days.

(21) Appl. No.: 17/291,478

(22) PCT Filed: Dec. 17, 2019

(86) PCT No.: PCT/SE2019/051297
§ 371 (c)(1),
(2) Date: May 5, 2021

(87) PCT Pub. No.: WO2020/139183
PCT Pub. Date: Jul. 2, 2020

(65) Prior Publication Data
US 2022/0000720 A1  Jan. 6, 2022

(30) Foreign Application Priority Data
Dec. 27, 2018  (SE) .................... 1851668-2

(51) Int. Cl.
A61J 17/00  (2006.01)
A61M 16/10  (2006.01)

(52) U.S. Cl.
CPC ........... *A61J 17/105* (2020.05); *A61J 17/001* (2015.05); *A61M 16/1045* (2013.01);
(Continued)

(58) Field of Classification Search
CPC .... A61J 17/105; A61J 17/001; A61J 2200/42; A61M 16/1045; A61M 16/105; A61M 2240/00; A61M 16/1055
(Continued)

(56) References Cited

U.S. PATENT DOCUMENTS 4,196,728 A     4/1980  Granite
4,878,496 A  *  11/1989 Chen ..................... A61J 17/001
                                                      606/234
(Continued)

FOREIGN PATENT DOCUMENTS

DE   9421156 U1    8/1995
EP   1625843 A1    2/2006
(Continued)

OTHER PUBLICATIONS

International Search Report PCT/ISA/210 for International Application No. PCT/SE2018/051297 dated Mar. 16, 2020.
(Continued)

Primary Examiner — Tuan V Nguyen
(74) Attorney, Agent, or Firm — Harness, Dickey & Pierce, P.L.C.

(57) ABSTRACT

A pacifier comprising a reusable suction part and at least one exchangeable housing part which are releasably connectable to each other, wherein said suction part comprises a nipple and a shield connected to each other, wherein said suction part comprises a passageway through which a fluid can pass from outside a mouth of a user of the pacifier to inside the mouth of the user of the pacifier, and wherein said suction part comprises at least one first connection device, and wherein said housing part comprises a housing and at least one second connection device which is releasably connectable to the at least one first connection device, wherein said housing comprises at least one heat and moisture exchanger (HME) device and/or at least one filter device.

13 Claims, 12 Drawing Sheets

(52) U.S. Cl.
CPC ...... *A61M 16/1055* (2013.01); *A61J 2200/42* (2013.01); *A61M 2205/7545* (2013.01); *A61M 2240/00* (2013.01)

(58) Field of Classification Search
USPC ........................................ 606/234, 235, 236
See application file for complete search history.

(56) References Cited

U.S. PATENT DOCUMENTS

| | | | |
|---|---|---|---|
| 5,211,656 A * | 5/1993 | Maddocks | A61J 17/113 606/236 |
| 5,435,298 A | 7/1995 | Anthony | |
| 6,110,193 A * | 8/2000 | Chen | A61J 7/0053 606/234 |
| 2003/0034031 A1* | 2/2003 | Lev | A61J 17/001 128/200.24 |
| 2007/0021782 A1* | 1/2007 | Inoue | A61J 17/001 606/234 |
| 2007/0021783 A1* | 1/2007 | Viana | A61J 7/0053 606/234 |
| 2012/0022446 A1 | 1/2012 | Desai et al. | |
| 2012/0277794 A1* | 11/2012 | Kountotsis | A61J 17/10 600/301 |
| 2013/0118485 A1* | 5/2013 | Shahaf | A61J 7/0053 128/202.16 |
| 2015/0051646 A1* | 2/2015 | Chan | A45F 5/02 606/236 |
| 2016/0256649 A1* | 9/2016 | Hesselmar | A61M 16/0468 |
| 2018/0333336 A1 | 11/2018 | Walker | |

FOREIGN PATENT DOCUMENTS

| | | |
|---|---|---|
| ES | 1059185 U | 3/2005 |
| GB | 2237208 A | 5/1991 |
| GB | 2353223 A | 2/2001 |
| GB | 2508020 A | 5/2014 |
| SE | 467685 B | 8/1992 |
| WO | WO-1999/11219 A1 | 3/1999 |
| WO | WO-2003/099366 A1 | 12/2003 |
| WO | WO-2007042765 A1 | 4/2007 |
| WO | WO-2015052121 A1 | 4/2015 |
| WO | WO-2015149127 A1 | 10/2015 |

OTHER PUBLICATIONS

Extended European Search Report dated Jul. 27, 2022 issued in corresponding European Appln. No. 19903956.1.
First Office Action issued Apr. 2, 2024 in Chinese Application No. 2019800862076.

* cited by examiner

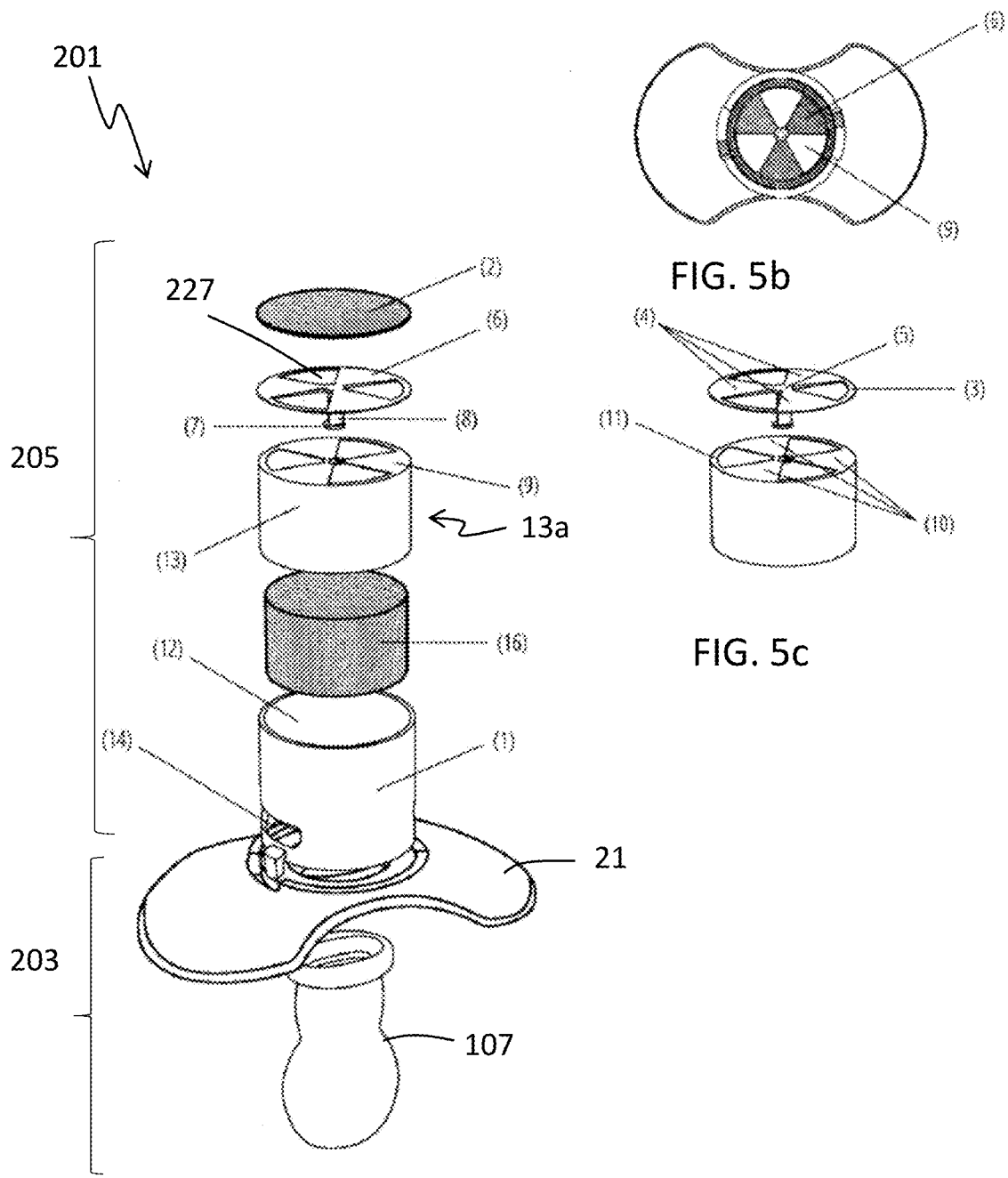

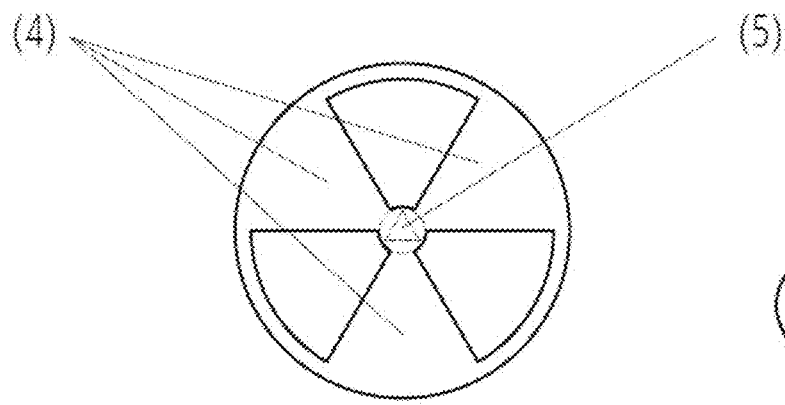
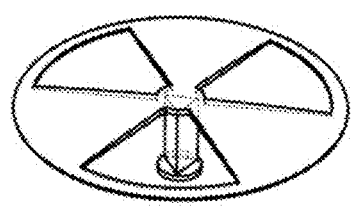
FIG. 6a
FIG. 6b
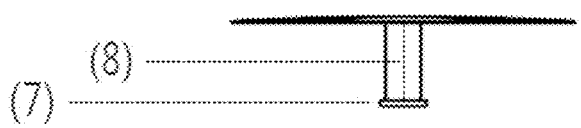
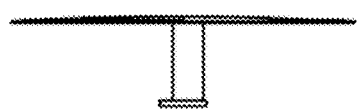
FIG. 6c
FIG. 6d

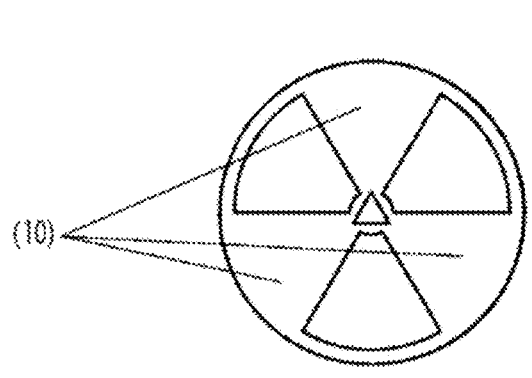
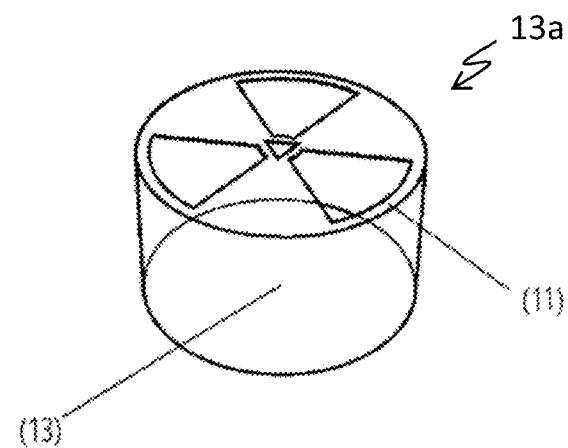
FIG. 7a    FIG. 7b
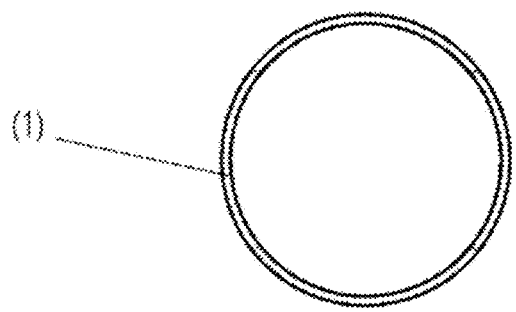
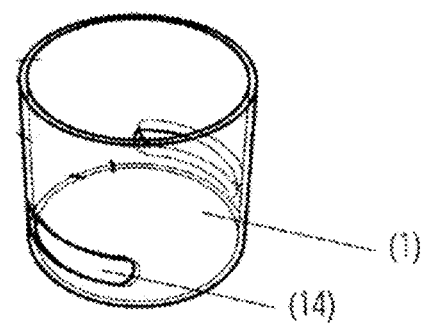
FIG. 8a    FIG. 8b
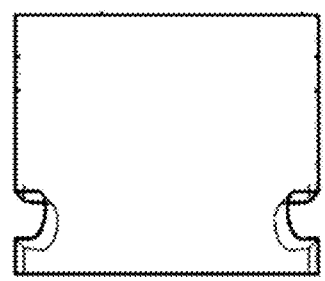
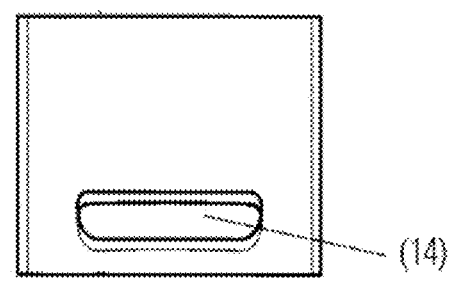
FIG. 8c    FIG. 8d

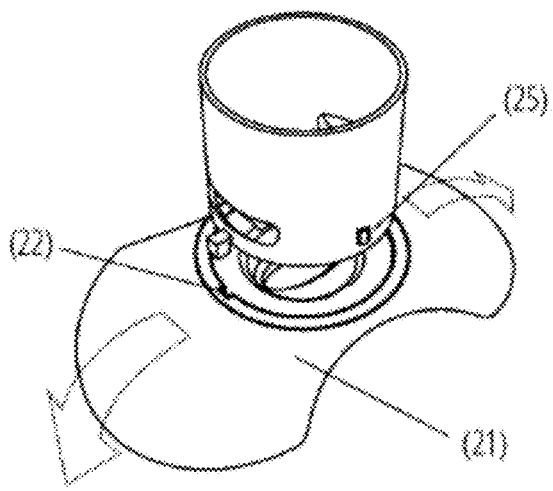
FIG. 11a
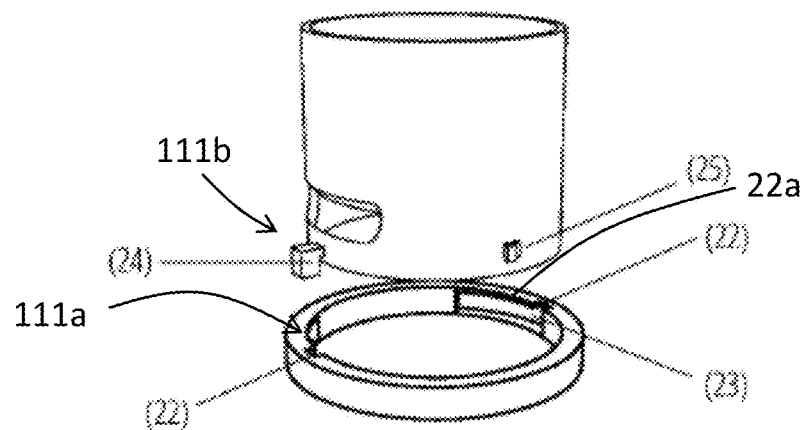
FIG. 11b
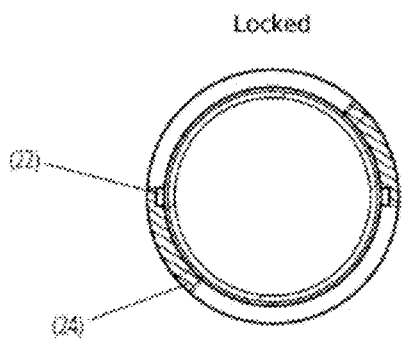 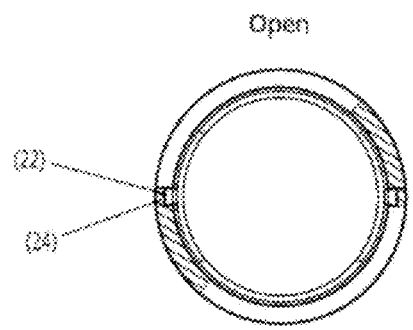
FIG. 11c  FIG. 11d

PACIFIER WITH FLUID PASSAGEWAY AND EXCHANGEABLE HOUSING

CROSS-REFERENCE TO RELATED APPLICATIONS

This application is a national phase under 35 U.S.C. § 371 of PCT International Application No. PCT/SE2019/051297, which has an International filing date of Dec. 17, 2019, which claims priority to Swedish Application No. 1851668-2, filed Dec. 27, 2018, the entire contents of each of which are hereby incorporated by reference.

TECHNICAL FIELD

The present invention relates to a pacifier, an exchangeable housing part configured to be used in a pacifier and to a pacifier system.

BACKGROUND

For many years, clean air was regarded as an unlimited resource. However, increasing global air pollution, has directed our attention to technologies related to the improvement of the air we breathe. In its simplest form, individuals in heavily polluted cities have become accustomed to avoiding being outdoors during certain hours of the day or periods of the year, or to wearing breathing masks similar to what is worn in hospitals to avoid infections to spread.

In humans, the nose receives and expels air for respiration alongside the mouth. Hair inside the nostrils will filter incoming air, as a first line of defence against dust particles, smoke, and other potential obstructions that would otherwise inhibit respiration, and as a kind of filter against airborne illness. In addition to acting as a filter, mucus contributes moisture to integral components of the respiratory system. The nasal area also heats the incoming air to optimal levels for the body. Thus, by acting as the first interface between the external environment and the delicate lungs, a human nose will condition incoming air, both as a function of thermal and moist regulation and filtration during respiration.

The mouth, on the other hand, is incapable of defending the lungs—breathing through the mouth will expose the lungs to polluted and/or infected air and will also expose the lungs to dry, cold air which can have detrimental effects, especially in small children.

EP 1 009 362 (Hadasit Medical Research) relates to a device that will enable its user to bypass any obstruction in the nasal airways and maintain an open channel to the ambient air. More specifically, this is achieved by providing a pacifier comprising: a nipple consisting of a nipple head and a nipple neck, a shield fixedly attached to, or integral with, said nipple neck, said nipple head being provided with at least one first opening adapted to communicate with the free atmosphere. Further, the pacifier is a breathe-through pacifier having an ambient air open channel between said at least one first opening and the atmosphere so that a user of the pacifier is able to inhale exclusively through the at least one first opening, sufficiently for breathing, whereby any obstruction in the nasal airways is bypassed. It is possible to provide the nipple with a one-way valve sensitive enough to respond to a minimal respiratory effort, but not permitting exhaled air to enter the nipple, thereby preventing the deposition therein of mucous substances. In this case, exhaled air will simply escape between the baby's lips and shield of the pacifier.

US2003034031 (Sleep Up Ltd.) describes a pacifier which facilitates mouth breathing. The pacifier is constructed such that sucking causes an air flow valve to assume a first operational state in which a channel of fluid communication is closed and cessation of sucking allows said air flow valve to assume a second operational state in which said channel of fluid communication is open.

Despite the available technology, there is still a need in the area of breath through pacifiers for improved devices, which are easy to use, not too costly to produce and which are capable of improving and conditioning inhaled air in multiple ways.

SUMMARY

An object of the present invention is to provide an improved pacifier.

A further object of the present invention is to provide a more versatile pacifier which will improve the quality of inhaled air.

This is achieved by a pacifier, an exchangeable housing part and a pacifier system according to the independent claims.

According to one aspect of the invention a pacifier comprising a reusable suction part and at least one exchangeable housing part which are releasably connectable to each other is provided, wherein said suction part comprises a nipple and a shield connected to each other, wherein said suction part comprises a passageway through which a fluid can pass from outside a mouth of a user of the pacifier to inside the mouth of the user of the pacifier, and wherein said suction part comprises at least one first connection device, and wherein said housing part comprises a housing and at least one second connection device which is releasably connectable to the at least one first connection device, wherein said housing comprises at least one heat and moisture exchanger (HME) device and/or at least one filter device.

According to another aspect of the invention an exchangeable housing part configured to be used in such a pacifier is provided, wherein said housing part comprises a housing and at least one second connection device which is releasably connectable to the at least one first connection device of the suction part, wherein said housing comprises at least one heat and moisture exchanger (HME) device and/or at least one filter device.

According to another aspect of the invention a pacifier system comprising a reusable suction part and at least two exchangeable housing parts according to any one of the preceding claims is provided.

Hereby a versatile pacifier is achieved. The suction part can be reused and connected to different housing parts. Hereby different types of filter devices and/or HME devices can be used together with the same suction part. Furthermore, when a filter device or HME device has been used some time it may be clogged and not effective anymore and needs to be changed. With this invention a new housing part with a fresh, unused filter device and/or HME device can easily be connected to the suction part.

The use of a HEM device inside the housing part of the pacifier will relive the child from the negative consequences of mouth breathing when nose breathing is inhibited for any reason. The HME, heat and moisture exchanger, device will prevent dehydration of the mouth and throat which causes discomfort. Furthermore, the HME prevents dry, cold air from reaching the lungs. This prevents several negative consequences, e.g. increased work of breathing, stagnation of mucus, lower oxygen levels among others.

The use of a filter device inside the housing part of the pacifier will reduce the amount of hazardous substances that a child might otherwise inhale in polluted environments. The type of filter device can be adopted to different environments with varying polluting toxic substances. Thanks to the releasably connected housing part the pacifier can be easily adopted for different situations and uses.

In some embodiments of the invention said passageway comprises a first end and a second end between which a fluid can pass, which first end is provided at a first connection interface of the suction part configured for mating with a second connection interface of the housing part and which second end of the passageway is provided in a part of the nipple which is configured to be positioned within a user's mouth during use of the pacifier, whereby a fluid can pass through the passageway between the first connection interface of the suction part and the inside of a user's mouth during use of the pacifier.

In some embodiments of the invention the housing of the housing part comprises an interior space which is defined by a lid, surrounding walls connected to the lid and a second connection interface which is provided opposite the lid, wherein said second connection interface is at least partly open into the interior space of the housing and is configured for mating with the first connection interface of the suction part.

In some embodiments of the invention the lid comprises air openings through which air can pass and wherein the HME device and/or the filter device are provided within the interior space of the housing such that air passing between the air openings in the lid and the second connection surface of the housing also has to pass the HME device and/or the filter device.

In some embodiments of the invention the HME device and/or the filter device is secured within the interior space of the housing by at least one grating which is welded to the surrounding walls.

In some embodiments of the invention the first or the second connection device comprises at least one recess and wherein the other one of the first or the second connection device comprises at least one protruding part whereby the at least one recess is configured to receive the at least one protruding part when the suction part and the housing part are connected.

In some embodiments of the invention the one of the first or second connection device comprising at least one recess further comprises a channel and a locking edge which are configured for allowing rotation of the housing part in relation to the suction part and locking of the protruding part.

In some embodiments of the invention the housing part further comprises a movable inner housing which is provided freely moving inside the housing and which in a first position will cover exhalation perforations provided in the housing and in a second position will not cover the exhalation perforations but instead cover inhalation openings provided in the housing.

In some embodiments of the invention said exhalation perforations are positioned in a surrounding wall of the housing such that exhaled air is directed toward a nose of the user of the pacifier.

Further embodiments are described in the dependent claims and in the detailed description.

BRIEF DESCRIPTION OF THE DRAWINGS

FIG. 5a is an exploded view of a pacifier according to one embodiment of the invention.

FIG. 5b is a top view of the pacifier as shown in FIG. 5a as assembled.

FIG. 5c shows a crown and a stem of the pacifier as shown in FIG. 5a.

FIGS. 6a-6d show the crown of the pacifier as shown in FIG. 5a in four different views.

FIGS. 7a-7b show the stem of the pacifier as shown in FIG. 5a in a top view and in a perspective side view.

FIGS. 8a-8d show a housing of the pacifier as shown in FIG. 5a in four different views.

FIGS. 11a, b, c and d illustrate how the housing of the pacifier may be attached through a locking mechanism, enabling easy removal and reattachment of said housing.

DETAILED DESCRIPTION OF EMBODIMENTS

FIGS. 1, 2, 3 and 4 show schematically pacifiers according to different embodiments of the invention which are very similar. Details which are the same are given the same reference numbers. FIGS. 5-13 show a pacifier and separate parts of this pacifier according to another embodiment of the invention. However, some features from the pacifier according to the embodiment as shown in FIGS. 5-13 can be implemented also in the other embodiments.

Figure 1A:
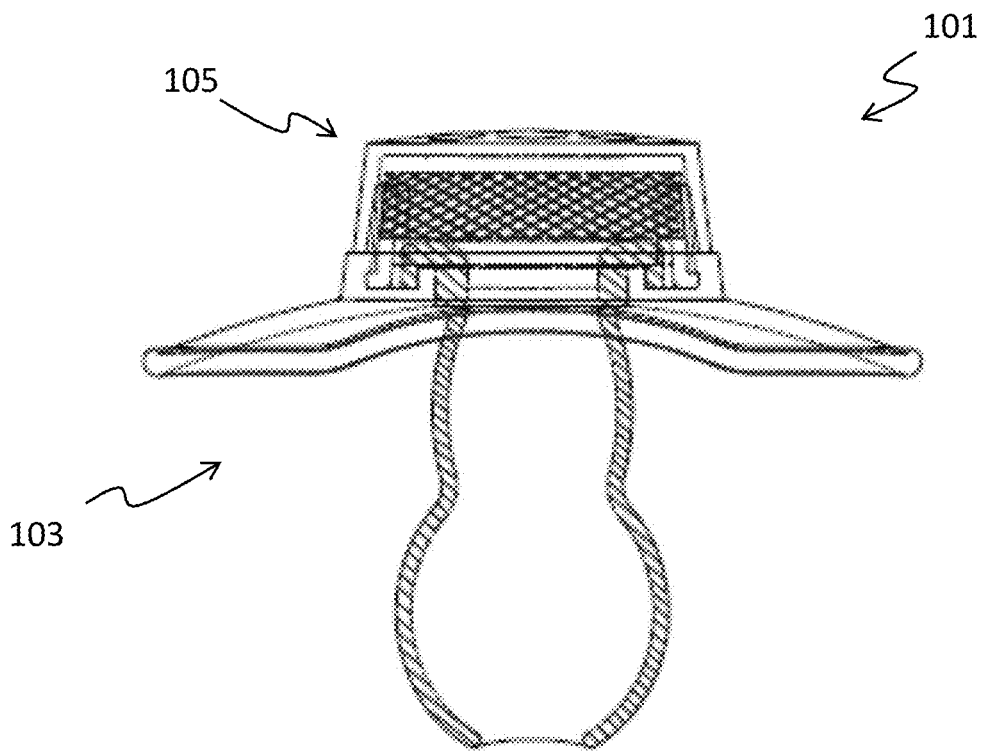
FIG. 1a shows schematically in cross section a pacifier according to one embodiment of the invention in an assembled position.
Figure 1B:
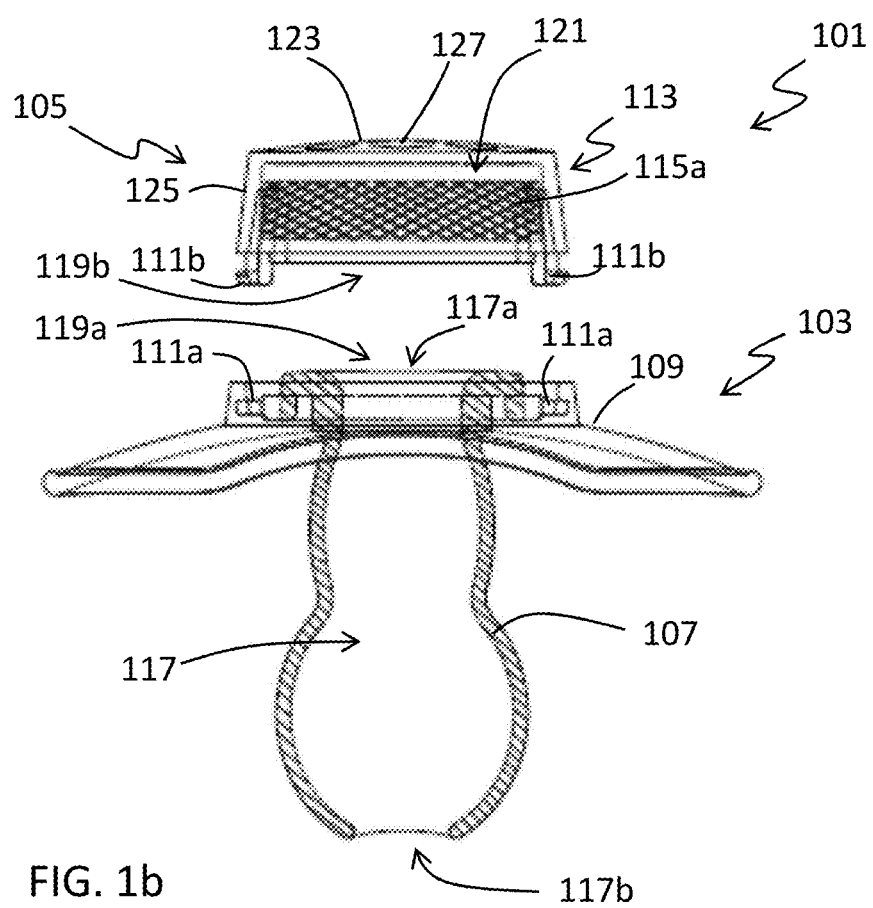
FIG. 1b shows the same pacifier as in FIG. 1a but in a separated position.
Figure 2A:
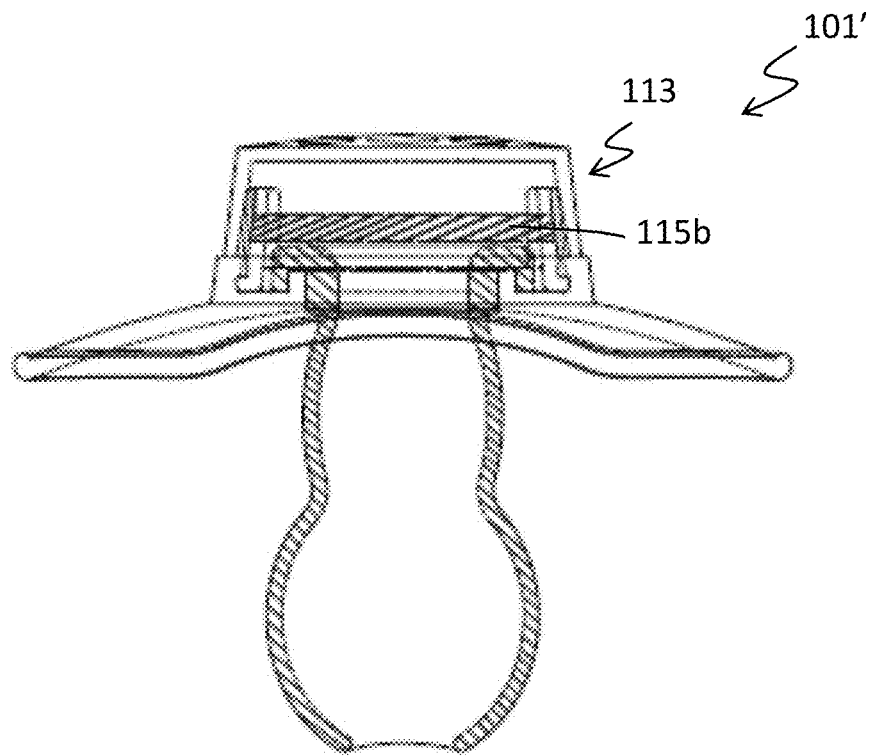
FIG. 2a shows schematically in cross section a pacifier according to another embodiment of the invention in an assembled position.
Figure 2B:
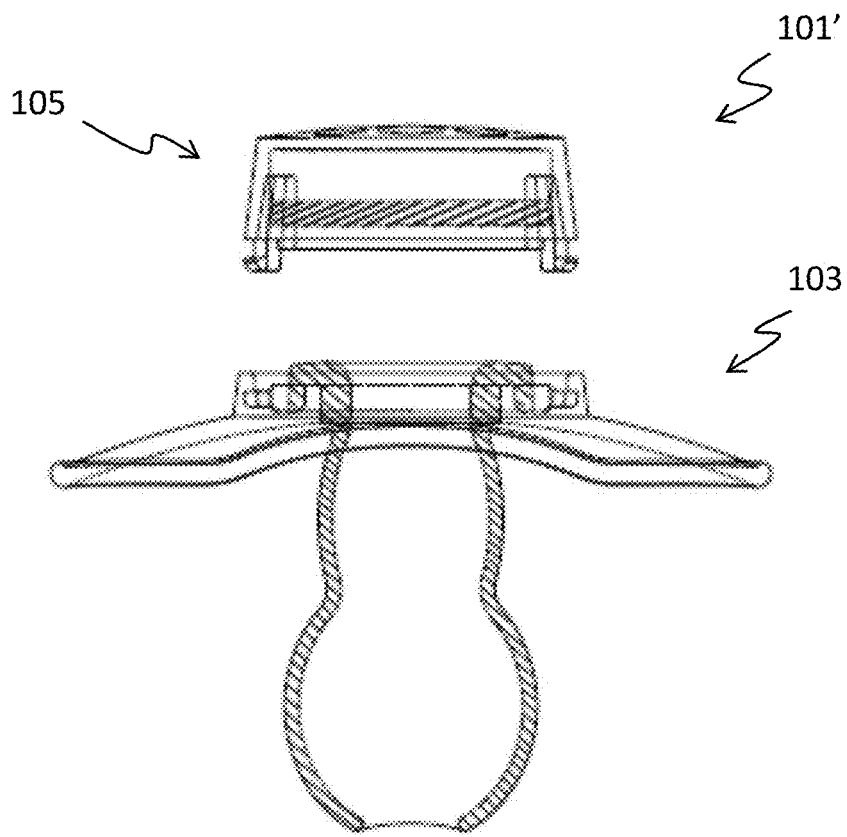
FIG. 2b shows the same pacifier as in FIG. 2a but in a separated position.
Figure 3:
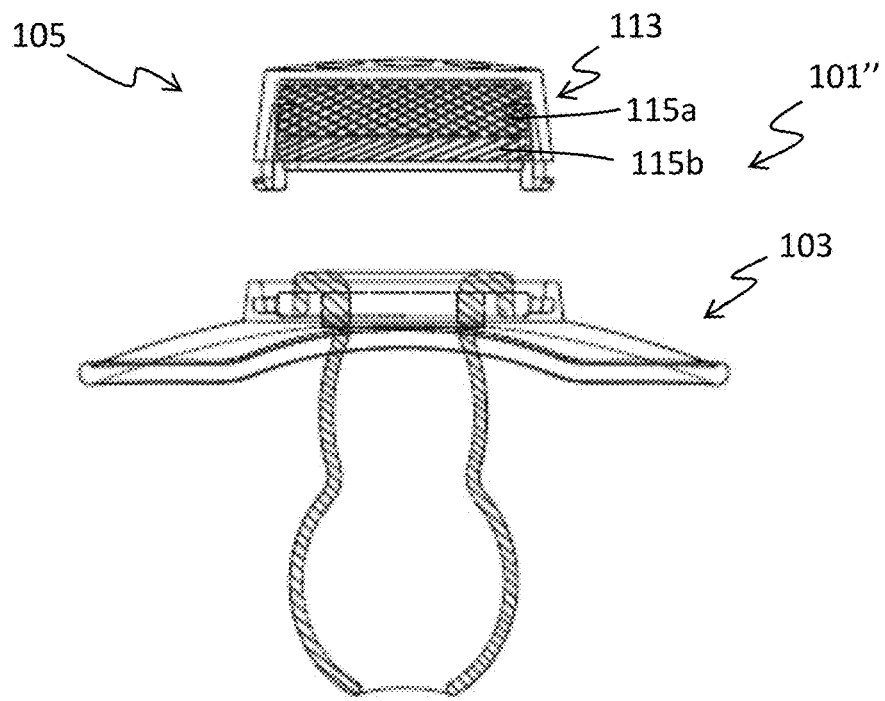
FIG. 3 shows schematically in cross section a pacifier according to another embodiment of the invention in a separated position.
Figure 4A:
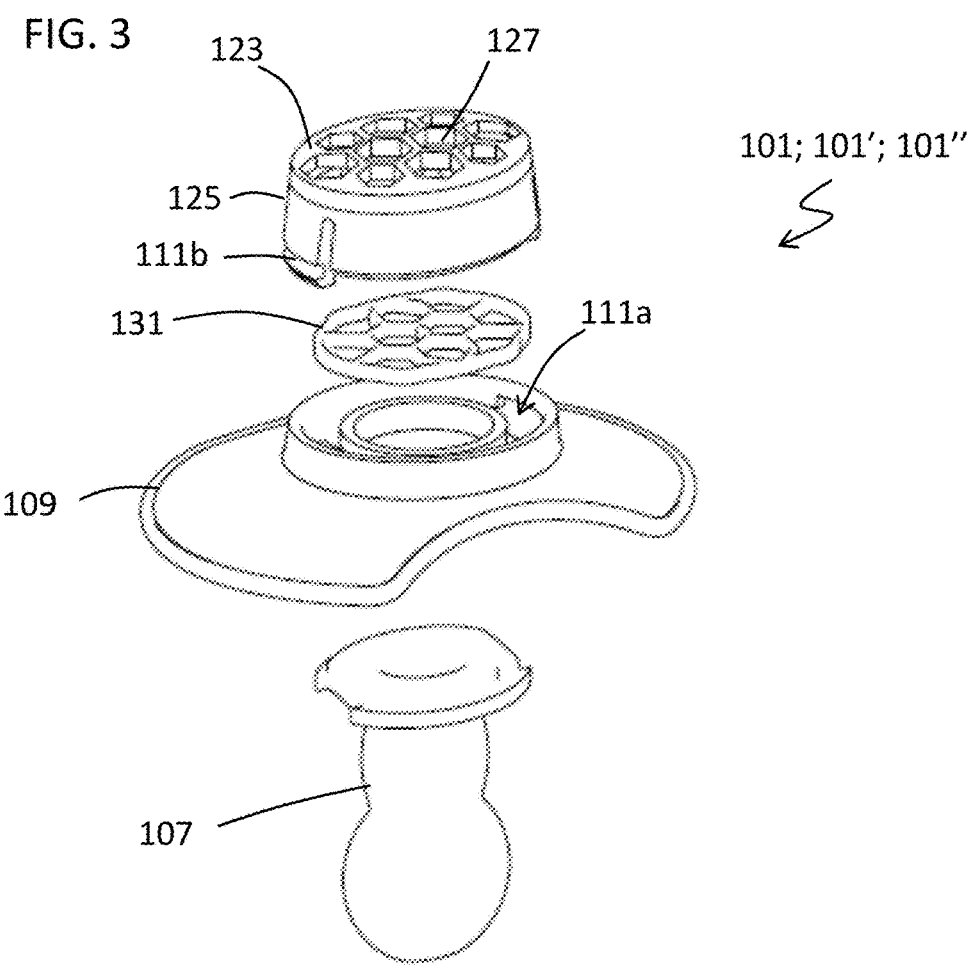
FIG. 4a is an exploded view of a pacifier according to one embodiment of the invention.

In FIGS. 1a and 1b a pacifier 101 according to one embodiment of the invention comprising a HME device 115a is shown in assembled (FIG. 1a) and separated (FIG. 1b) positions. In FIGS. 2a and 2b a pacifier 101' according to another but similar embodiment of the invention comprising a filter device 115*b* is shown in assembled (FIG. 2*a*) and separated (FIG. 2*b*) positions. In FIG. 3 a pacifier 101" according to another embodiment of the invention comprising both a HME device 115*a* and a filter device 115*b* is shown in separated position. FIG. 4*a* shows a pacifier according to one embodiment of the invention in exploded view. This could be any of the embodiments as shown in FIGS. 1-3. No filter device or HME device is shown in FIG. 4*a*. All these embodiments will now be described together referring to FIGS. 1-4.

According to the invention a pacifier 101; 101'; 101" is provided which comprises a reusable suction part 103 and at least one exchangeable housing part 105 which are releasably connectable to each other. A pacifier system can also be provided according to the invention comprising one suction part 103 and more than one housing parts 105 which are intended for use with the same suction part 103. Hereby the suction part 103 can be reused together with different housing parts 105. The housing parts 105 can be changed due to a need for changing or cleaning of the HME device 115*a* or filter device 115*b* provided therein or because there is a need for another type of HME device 115*a* or filter device 115*b*. Hereby the pacifier 101; 101'; 101" can be delivered as a kit with one suction part 103 and a number of housing parts 105. As a first option in this invention it is intended that the housing part is completely exchanged, i.e. the housing part is a single use part which is disposed after use. However, alternatively, instead of changing the whole housing part, the housing part can be released from the suction part and the filter device and/or HME device can be changed to a new one or cleaned for reuse.

The suction part 103 comprises a nipple 107 and a shield 109 connected to each other. The nipple 107 is configured to be sucked by a child and the shield 109 is provided for preventing swallowing of the nipple 107 as is common for pacifiers. According to the invention the suction part 103 comprises a passageway 117 through which a fluid can pass from outside a mouth of a user of the pacifier 101; 101'; 101" to inside the mouth of the user of the pacifier. Hereby the pacifier 101; 101'; 101" is a breath-through pacifier which is suitable to use for example when nose breathing is inhibited.

The suction part 103 comprises furthermore at least one first connection device 111*a* for connection with the housing part 105. The housing part 105 comprises a housing 113 and at least one second connection device 111*b* which is releasably connectable to the at least one first connection device 111*a*. In this embodiment the first connection device 111*a* comprises two opposing recesses and the second connection device 111*b* comprises two protruding parts, whereby the recesses are configured to receive the protruding parts when the suction part 103 and the housing part 105 are connected. For allowing the protruding parts to enter the recesses the protruding parts may be resilient. Another alternative is that for example the shield 109 is resilient and can be bent to allow the protruding parts to enter into the recesses. A still further alternative is shown in relation to FIG. 4*b* and will be further described below. In the embodiment described in relation to FIG. 4*b* the protruding parts do not need to be resilient. The number of recesses and protruding parts can of course be another than two. Furthermore, the recesses could as well be provided in the housing part 105 and the protruding parts in the suction part 103. For improving the connection and securing the connection a rotational locking feature can as well be provided. By rotating the housing part 105 in relation to the suction part 103 when they have been connected the first and second connection devices 111*a*, 111*b* can be provided in a locking position. For example the recesses can be provided as grooves allowing protruding parts to be guided in the grooves when the housing part is rotated. One example of a rotational locking feature which can be used also in this embodiment of the pacifier is shown in FIGS. 11*a*-11*d*.

Figure 4B:
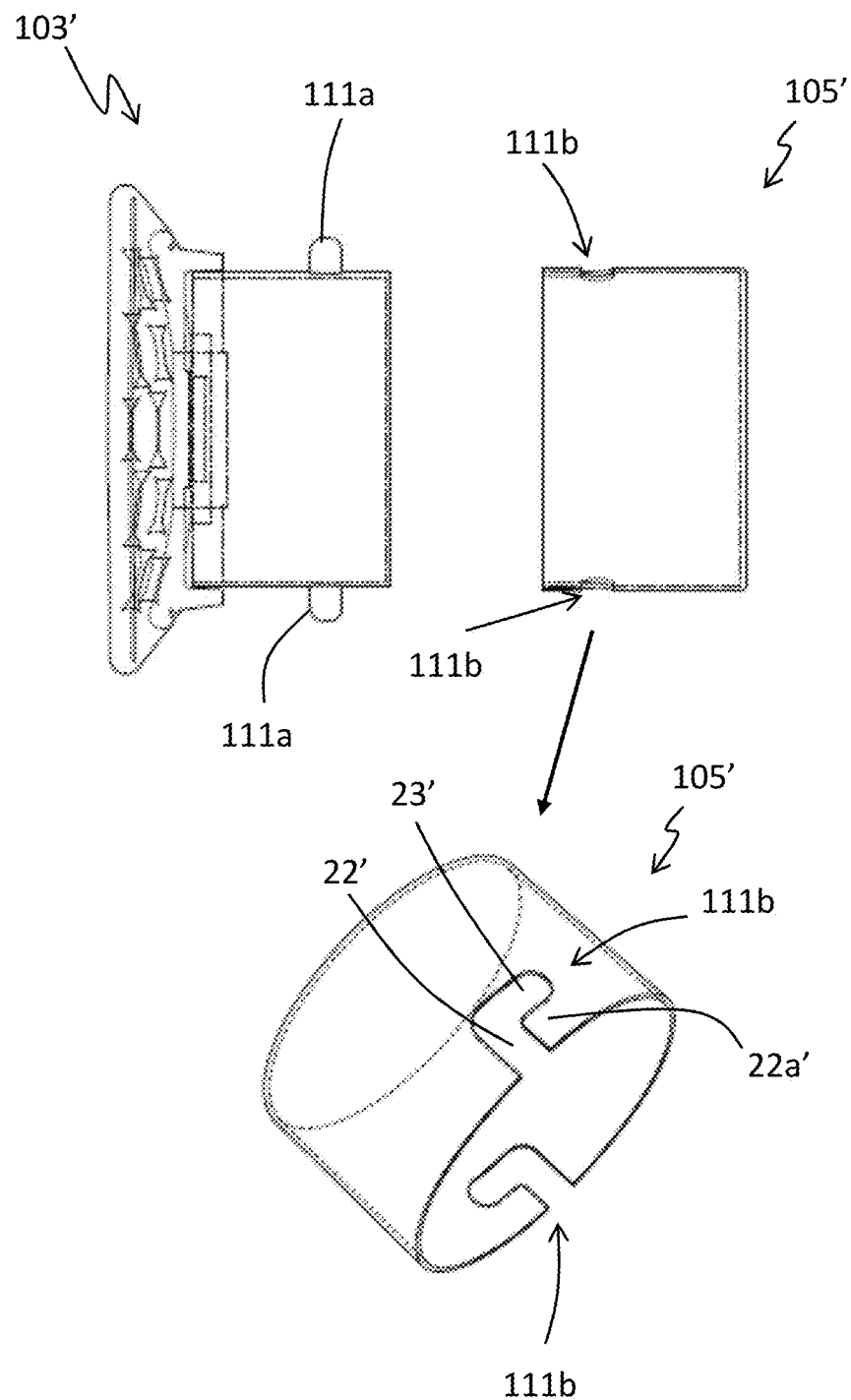
FIG. 4b shows a connection mechanism which can be used for connecting a suction part and a housing part of a pacifier according to one embodiment of the invention.

An alternative connection and locking mechanism which can be used for connecting a suction part 103' (nipple not shown in this view) and a housing part 105' of a pacifier according to the invention is shown in FIG. 4*b*. In this embodiment of the locking mechanism a first connection device 111*a* provided in the suction part 103' comprises two protruding parts (however, the number of protruding parts can of course be varied). A second connection device 111*b* is provided in the housing part 105' and comprises two recesses 22' for receiving the protruding parts and a channel 23' into which the protruding parts 111*a* can be rotated, i.e. the recesses and channels allows rotation of the housing part in relation to the suction part when the protruding parts have been received in the recesses. A locking edge 22*a*' locks the protruding parts 111*a* within the channels 23'. The dimensions of the protruding parts 111*a*, the recesses 22' and the channels 23' can be provided such that friction between the parts keeps them connected to a requested strength but allows disengaging of the two parts. Furthermore, an inward angle of the channel 23' in relation to the recess 22' or an additional channel directed inwards can be adopted such that the housing part 105' needs to be pushed towards the somewhat inertially recoiling suction part 103' for allowing the rotation of the protruding parts 111*b* in the channels 23'. The channel thus forms more of a "U"-shape, with the tips of the U directed towards the suction part 103'.

According to the invention said housing 113 comprises at least one heat and moisture exchanger (HME) device 115*a* and/or at least one filter device 115*b*. In the embodiment as shown in FIGS. 1*a* and 1*b* the housing 113 comprises only a HME device 115*a*. In the embodiment as shown in FIGS. 2*a* and 2*b* the housing 113 comprises only a filter device 115*b* and in the embodiment as shown in FIG. 3 the housing 113 comprises both a HME device 115*a* and a filter device 115*b*.

The passageway 117 comprises a first end 117*a* and a second end 117*b* between which a fluid can pass, which first end 117*a* is provided at a first connection interface 119*a* of the suction part 103 which is configured for mating with a second connection interface 119*b* of the housing part 105. The second end 117*b* of the passageway 117 is provided in a part of the nipple 107 which is configured to be positioned within a user's mouth during use of the pacifier 101; 101'; 101", whereby a fluid can pass through the passageway 117 between the first connection interface 119*a* of the suction part 103 and the inside of a user's mouth during use of the pacifier. The passageway 117 is hereby extending through the nipple 107 and through the shield 109.

The housing 113 of the housing part 105 comprises an interior space 121 which is defined by a lid 123, surrounding walls 125 connected to the lid 123 and the second connection interface 119*b* which is provided opposite the lid 123. Said second connection interface 119*b* is at least partly open into the interior space 121 of the housing 113 and is configured for mating with the first connection interface 119*a* of the suction part 103.

Furthermore, the lid 123 comprises air openings 127 through which air can pass. The HME device 115*a* and/or the filter device 115*b* are provided within the interior space 121 of the housing 113 such that air passing between the air openings 127 in the lid 123 and the second connection surface 119b of the housing 113 also has to pass the HME device 115a and/or the filter device 115b.

In some embodiments the HME device 115a and/or the filter device 115b can be secured within the interior space 121 of the housing 113 by at least one grating 131 which is welded to the surrounding walls 125. Such a grating is shown in FIG. 4a.

Another embodiment of the invention will now be described with reference to FIGS. 5-13. A pacifier 201 according to one embodiment of the invention is shown in exploded view in FIG. 5a and separate parts of this pacifier 201 are shown in the drawings 5b, 5c, 6, 7, 8 and 11. FIGS. 9, 10, 12 and 13 shows the pacifier 201 in different positions. Like the previous described embodiments, the pacifier 201 according to this embodiment of the invention comprises a reusable suction part 203 and at least one exchangeable housing part 205 which are releasably connectable to each other.

The suction part 203 comprises a nipple 107 and a shield 21 connected to each other, wherein said suction part 203 comprises a passageway 117 through which a fluid can pass from outside a mouth of a user of the pacifier to inside the mouth of the user of the pacifier. Said suction part 203 comprises at least one first connection device 22. Said housing part 205 comprises a housing 1 and at least one second connection device 24 which is releasably connectable to the at least one first connection device 22. Said housing 1 comprises one or more of: a heat and moisture exchanger (HME) device 16 and a filter device 2. In the embodiment shown in FIGS. 5-13 a filter device 2 is shown to be provided as a top layer of the housing part 205. However, the filter device 2 could also in this embodiment be provided inside the housing 1 as in the embodiment described in relation to FIGS. 1-4.

Figure 9A:
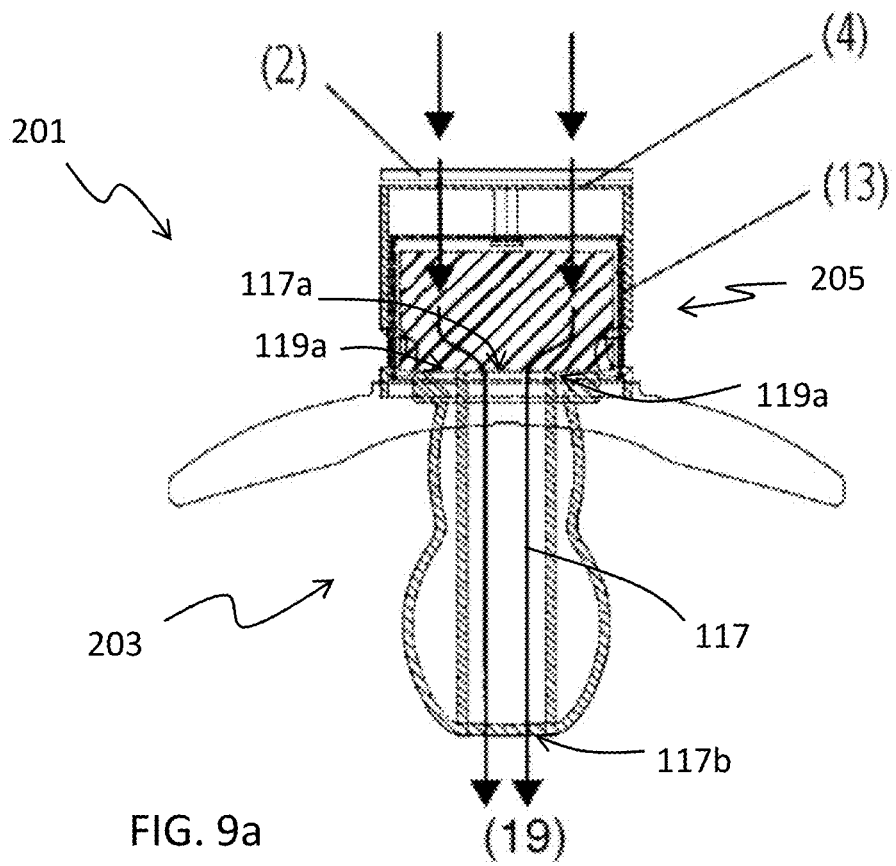
FIGS. 9a-9b are detailed views of how an illustrative device according to the embodiment of the invention as shown in FIG. 5a may be arranged to include HME device 16, a filter device 2 and diverting channels. In addition, it appears from the arrows how airstreams may be directed for inhalation as well as exhalation.

The passageway 117 comprises a first end 117a and a second end 117b between which a fluid can pass (can be seen in FIG. 9a). The first end 117a is provided at a first connection interface 119a of the suction part 203 configured for mating with a second connection interface 119b of the housing part 205 and the second end 117b of the passageway 117 is provided in a part of the nipple 107 which is configured to be positioned within a user's mouth during use of the pacifier 201, whereby a fluid can pass through the passageway 117 between the first connection interface 119a of the suction part 203 and the inside of a user's mouth during use of the pacifier. The passageway is hereby extending through the nipple 107 and through the shield 21.

The housing 1 may be of a shape which is ergonomically adapted to its intended use, as will be discussed in more detail below. The skilled person would appreciate that e.g. any plastic may be useful, as long as there is no leakage of chemicals and/or unpleasant taste to the user. The housing may e.g. be essentially circular, and provided as appropriate with openings for air passage, such as perforations, and one or more valves, as will be discussed in more detail below.

Further, the housing 1 of the pacifier 201 may include one or more membranes to enable a valve function when combined in moving engagement with an appropriately arranged disk: By openings in such a disk, a valve function is created during breathing as the membrane will then move towards the user, to open the passage of air, as a result of the pressure. As the skilled person will appreciate, the 'moving engagement' here refers to a possibility of shifting between an open position where air can pass during inhalation; and a closed position during exhalation.

Thus, more specifically, the housing 1 of this embodiment of the present invention enables a valve function through a combination of one moving part (including membranes designed as leaves and a stem) and one fixed part relative to the before mentioned (a crown), both arranged within the same cylindrical part, as will appear from the description of the drawings below. This design offers several advantages, such as to protect the filter from humidification and thus increasing its usefulness and life length; to enable compression of the HME ridding it from any mucus or secretions which would otherwise reduce its usefulness; and to enable air to be inhaled via the outermost filter device only, to ensure its purity. Furthermore, this design enables the creation of a conditioned microclimate around the user's respiratory orifices, using inhalation and exhalation, allowing the user to breathe conditioned air through both the mouth and nose, without any mechanical manipulation of the nose of the user. This is a clear advantage, especially when dealing with small infants.

The description of the specific embodiment as shown in FIGS. 5-13 is continued below, however some of the details around for example the HME device 115a; 16 and the filter device 115b; 2 will be relevant also for the previously described embodiment as described in relation to FIGS. 1-4.

HME materials are widely used in the area of artificial noses. An International Standard (ISO 9360) specifies the properties of HMEs and defines it as a "device intended to retain a portion of the patient's expired moisture and heat and return it to the respiratory tract during inspiration". The material which constitutes the active part of the HME is often referred to as the exchange medium or membrane. This medium consists of a range of materials, such as cellulose, polymeric foam, metal fibres, ceramic or paper. The medium is often treated with a desiccant, e.g. calcium or lithium chloride, and may exhibit different characteristics depending on the intentions of the manufacturer.

In addition to the above-mentioned medical contexts, HME materials are also used in other situations when deficiencies in air moisture dry out the airways and thicken the secretions, causes ciliary damage along with discomfort. However, it is also well known that wet HMEs increases the work of breathing, making their arrangement in breathing aids important.

In the embodiment of the invention as shown in FIGS. 5-13, said HME device 16 is arranged closer to the mouth of the individual than the filter device 2, which enables the removal of excess humidity from the HME device 16 before exhaled air reaches the filter device 2. Thus, a pacifier according to some embodiments of the invention may comprise a HME device arranged to be accessible in use for regeneration thereof by manual compression.

More specifically, the pacifier according to the invention may comprise means to divert moisture or liquid originating from compression of said HME device 16 and/or exhaled air from passing the filter device 2. As the skilled person will appreciate, the humidity of the exhaled air could otherwise have a negative impact on the filter. Diverted liquid may be allowed to exit the housing e.g. via slits, perforations or other suitable openings or valves, and such liquid may be directed towards a desired location.

Further, a pacifier according to the invention may comprise means to divert exhaled and/or inhaled air, such as slits or perforations, as outlined in more detail in the drawings.

Furthermore, the pacifier according to the invention may comprise means to condition air inhaled solely through the nose through filter means arranged outside of the housing. The pacifier according to the invention may comprise an outer design that affects the airflow around the device by influencing the airflow created by respiratory efforts.

In order to facilitate the breathing of an individual, the inlet for the airflow through the housing may be designed specifically for optimal airflow and minimal resistance. A device according to the invention may comprise means specifically shaped for adaptation to the characteristics of the oral area of a human individual.

Various diverting and other designs will be explained in more detail in the context of the drawings 5-13 provided below.

As appears from the above, the pacifier 101; 101'; 101''; 201 according to the invention (both the embodiment as shown in FIGS. 1-4 and the embodiment as shown in FIGS. 5-13) may comprise one or more filter devices 115b; 2, such as at least one chemical or mechanical filter. Such filters may be any kind of conventionally used bacterial and/or particulate filter. The filter device can for example be a pleated filter or an electrostatical filter. In order to purify the inhaled air from unpleasant or harmful particles, a pacifier according to the invention may comprise a particulate filter defined by a cut-off of about 2.5 µm, such as in the range of 0.1-10 µm.

The filter device 115b; 2 may be arranged in a circular manner to align with the cross section of an e.g. cylindrical housing 113; 1. In the embodiment as shown in FIGS. 5-13 the filter device 2 may be located at the far end of the device i.e. further away from the user's mouth than the HME device 16.

More specifically, the filter device 115b; 2 is arranged in the pacifier 101; 101'; 101''; 201 of the present invention to remove minute hazardous particles, generated by industry, combustion engines and other human activity associated with pollution. Particulate matter is a heterogeneous mixture composed of carbonaceous combustion materials such as polycyclic aromatic hydrocarbons, biogenic material, salts, and other inorganic materials such as transition metals. The sizes of such particles can be divided into 10 PM (2.5-10 um) 2.5 PM (0.1-2.5 um) or ultra-fine particles (<0.1 um).

It is well known that the process of filtration is complicated and various filters exists on the market today, covering a broad range of applications such as, but not limited to, respiratory protection, air cleaning of smaller effluents, processing of hazardous materials, removal of asbestos fibres and diesel particles.

Mechanical filters are commonly divided into membrane filters and fibrous filters. The properties and performances of these filters vary widely depending on intended use. Important aspects of filters in the present context are their efficiency regarding removal of certain particle sizes and their performance when wet. For humans holds generally that the smaller the particle, the further down into the respiratory tract it will travel. The device herein described is not limited to any particular filter type, but can be adapted to suit different filters depending on the desired application. One illustrative particle filter which is commercially available is the 3M™ Particulate Respirator 8670F. This is a FDA approved filter intended for use by the general public to reduce exposure to airborne particles.

Thus, the invention according to the embodiment as shown in FIGS. 5-13 relates to the use of filter device 2 combined with openings in a housing 1 and/or air directing channels in its structure. This conditions the air around the user's respiratory orifices using both cleaned conditioned inhaled and exhaled air as follows. During inspiration polluted air moves through the filter device 2 and is cleaned. This clean air moves further through the HME device 16 and down to the respiratory tract. During exhalation clean air from the user's respiratory tract is diverted through openings/perforations 14 (further described below in relation to FIG. 8) in the housing 1 in such a fashion that it dilutes polluted air around the user's respiratory orifices, and this clean air can subsequently be inhaled. The experienced expert may raise the question of oxygenation and/or rebreathing issues. This is regarded negligible considering the vast amount of surrounding air and fast diffusion of molecules in air. The airstreams and microclimate around the user can be visualised through specific simulation techniques in addition to technical experiments. Using experimental testing in a laboratory the contents of the air and air flows can be measured and visualised utilizing Computational Fluid Dynamics (CFD). This technique can thereafter be combined with computer simulations in order to calculate and produce the exact and optimal composition of the filter means and also for guidance in how to optimise airflows to establish a conditioned air pocket around the desired area, i.e. the mouth and nose orifices. The CFD technique can also be used to trace velocities and the distribution of particles and contaminations to demonstrate and validate the function and uniqueness of the device.

The above-mentioned resistance that appears when breathing through active HME materials may sometimes appear as a larger problem with young infants and children than with adults, who are aware of the advantages of its use. However, to the experienced expert in the field this is not an effect to shun from as described below. The present invention has proved to be advantageous in this respect. The present invention combines several functions to optimise and resemble normal breathing physiology, especially important in infants. The HME provides for humidity, purification and warming of inhaled air. The resistance that occurs when breathing through the HME device and filter device is of benefit in exhalation as this increases the end expiratory pressure, which in turn keeps the lungs of the user more open and has positive effects on oxygenation. This principle is widely used in healthcare to improve oxygenation in patients, especially if the airways have been compromised with a breathing tube. Thus, this effect is consciously aimed at in this embodiment of the present device.

According to this embodiment of the invention the housing part 205 comprises a movable inner housing 13a which is provided freely moving inside the housing 1 and which in a first position will cover exhalation perforations 14 provided in the housing 1 and in a second position will not cover the exhalation perforations 14 but instead cover inhalation openings 227 provided in the housing 1. Suitably said exhalation perforations 14 are positioned in a surrounding wall of the housing 1 such that exhaled air is directed toward a nose of the user of the pacifier. Hereby the freely moving inner housing 13a will during inhalation be drawn closer to the mouth of the user and hereby cover the exhalation perforations 14 and hereby prevent air from entering into the users mouth through the exhalation perforations 14. During exhalation the inner housing 13a will be forced outwards, i.e. in a direction out from the mouth of the user and hereby the exhalation perforations 14 will be opened up and allow exhalation air to exit therethrough.

The invention also relates to a locking mechanism arranged between the housing part 205 and the suction part 203, or more specifically between the housing 1 and the shield 21, enabling safe exchange of the housing part 205 including the filters. The locking mechanism may be arranged as a feature of a device according to the invention and enables an easy change of the filter device and HME device, which are known to have a limited life span.

This changeability also enables the possibility to use different filter types according to the needs of the user, e.g.

depending on pollution type. One advantage of the invention is that such locking is easily designed as child proof, but at the same time intuitively easy for an adult to change. The housing 1 is locked in place in the shield 21 which has slits 22 (which is a part of a first connection device 111*a*) while small spikes 24 (corresponding to a second connection device 111*b*) are situated on the housing 1. To remove the housing 1 the shield 21 has to be bent in accordance to its curvature, enabling rotation of the housing 1, which when rotated removes the spikes 24 from the slits 22, enabling removal of the housing 1. To reassemble the device the shield 21 is bent and the housing 1 re-attached and rotated back again. Thereafter the shield 21 is released which causes it to slightly straighten out through its innate rigidity, locking the housing 1 from rotation via a locking edge 22*a* on the slit 22 in the shield 21.

Thus, the invention relates to a device as described above, which comprises means to assemble and disassemble the housing part 105; 205 from the suction part 103; 203 in a child proof manner, enabling switching of the filter device and HME device, hence optimizing the function of the device.

With reference to FIGS. 5-8, the invention will be described by an example where all parts are arranged inside a cylindrical housing 1. From outside towards the mouth of the user, firstly a filter device 2, e.g. as described above, is attached to the housing 1. Below this filter device 2 is a circular movable piece 3, as wide as the inner diameter of the walls of the housing 1 to provide a substantially air and liquid tight sealing, with three spokes 4, which are adjoined in the middle of the ring, here exemplified as a circular hub 5, all parts 3-5 together forming a crown 6, On the inner part of the hub 5 is a short knob 7, i.e. pointing inwards. The short shaft 8 is not cylindrical, but can be any other shape, e.g. triangular, to prevent rotation of the crown 6 relative to the leaves 10. Attached to the knob 7, but freely movable along its length up or down is a thin, but air and liquid proof circular (or any other geometric shape corresponding to the housing 1 and crown 6) membrane 9, as wide as the inner diameter of the housing 1. This membrane 9 is perforated with its openings corresponding to the spokes 4 of the crown. And vice versa the leaves of the membrane overlap the perforations in the crown. This enables inhalation of air as the leaves 10 will move inwards, exposing the holes in the crown 6. As expiration begins the air will push the leaves 10 outwards, closing the openings which prohibit air from flowing outwards this way. At their outermost part the leaves 10 are conjoined in a ring 11, as wide as the inner diameter of the housing 1. This ring 11 continues downward along the inside part 12 of the housing, thus comprising a slightly smaller and much thinner, cylinder itself, this is called the stem 13. In the housing cylinder 1, there are perforations 14 allowing outwards air passage 20. As the stem 13 moves with the leaves 10 outwards in exhalation these perforations 14 will be exposed and air flow is possible outwards. These airflows are controlled through the shape of the openings and other aerodynamic modulations, e.g. directed in an upwards fashion towards where the user's nose will be situated. As the leaves 10 moves inwards during inspiration the stem 13 moves downwards within the housing 1, covering the perforations 14 prohibiting air to enter the housing this way. The HME device 16 is placed inside and proximal of the stem 13, and since all the inner parts 3,13 are movable in regard to the inner surface 12 of the housing 1, the HME device 16 can be compressed via external manual pressure on the crown 6. Thus enabling refreshment and regeneration of the HME device when moist (se also FIG. 10). This possibility to compress the HME device requires that the walls of the stem 13 are soft and compressible to some extent, see FIG. 10.

Figure 9B:
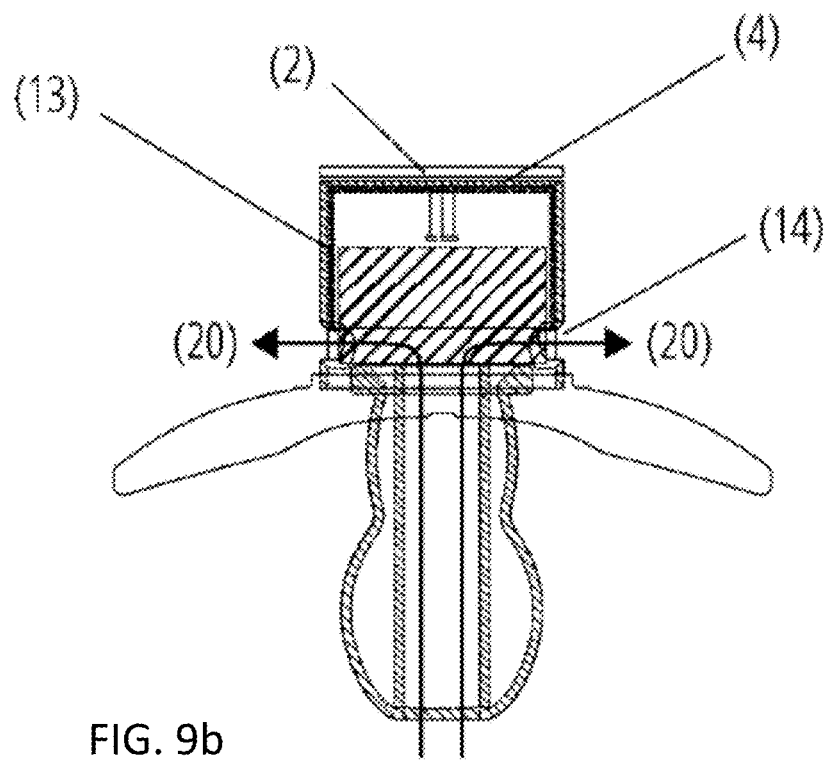

FIGS. 9*a-b* describe the valve mechanism and the diverting of airstreams in detail. At the beginning of inhalation the leaves 10 moves inwards as seen in 9*a* allowing air to be inhaled 19 via the pacifier. FIG. 9*b* describes the valve function during exhalation. The leaves 10 and stem 13 has moved outwards blocking air passage through the filter device 2. The exhaled air 20 exits the housing 1 via perforations 14, protecting the filter device from moist. This exhaled air is directed towards a desired location (e.g. the nose of the user), allowing for dilution of polluted air with clean air.

Figures 10A, 10B:
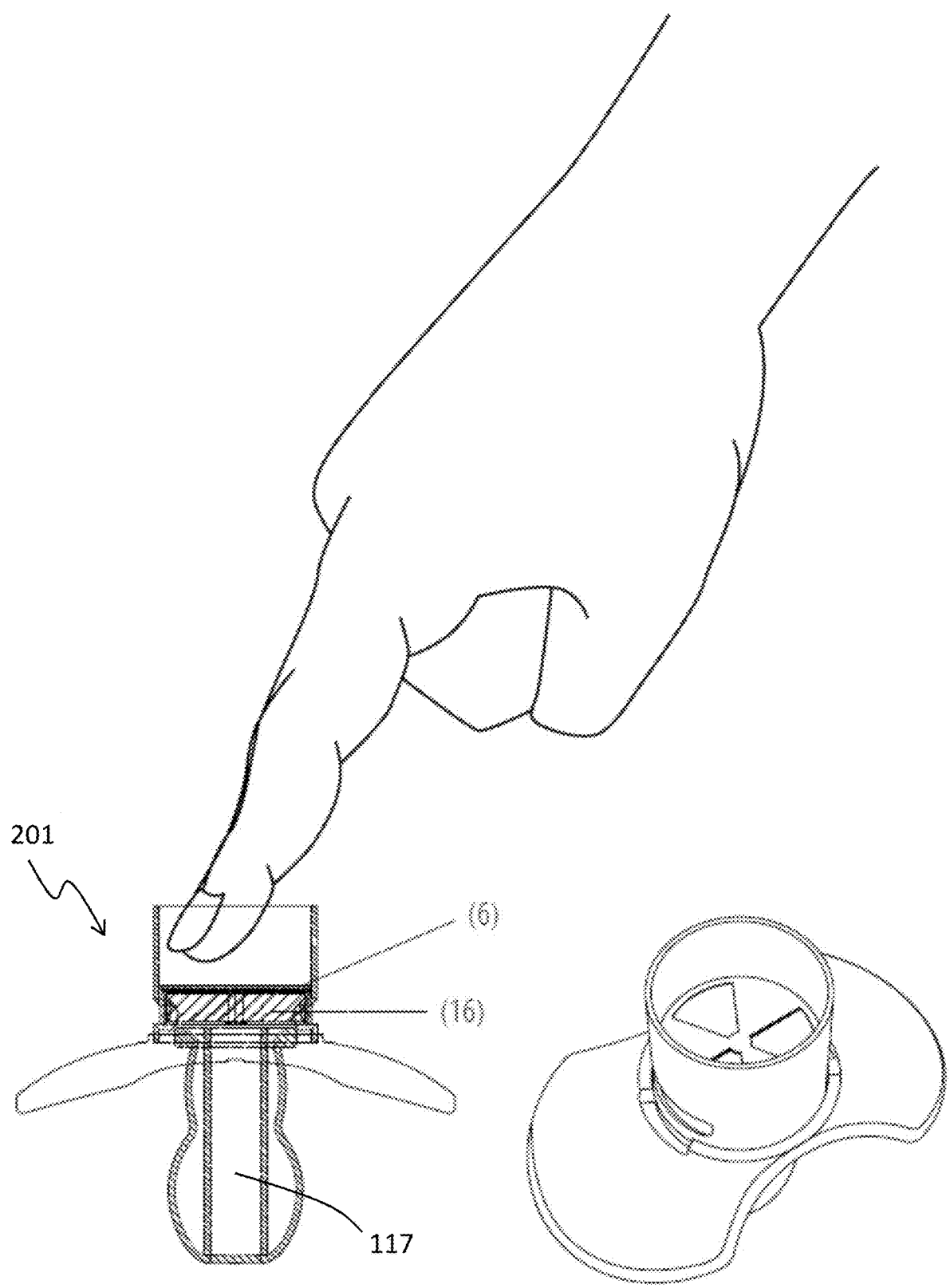
FIGS. 10a-10b are illustrative views of how the pacifier according to the embodiment as shown in FIG. 5a may be provided with a plate accessible for manual compression to remove humidity and hence regenerate the HME device.

FIG. 10 depicts how the HME device 16 is refreshed via manual compression. Pressure on the crown 6 will compress the HME device, ridding it of excess moisture, which is expelled through the perforation in the teat of the pacifier (through the passageway 117 in the suction part 203). The internal elasticity of the HME device causes it to regain its ordinary shape after ending compression, resetting the device to its original state.

FIGS. 11*a*-11*d* describe the locking mechanism for the housing 1 in the shield 21 (housing part 205 in the suction part 203) of the device. In FIG. 11*a* the shield 21 is bent according to its curvature, exposing the small slits 22 (which is a part of the first connection device 111*a*, which in this embodiment further comprises channels 23) which enables fitting of the spikes 24 (corresponding to the second connection device 111*b*) in the housing 1. This allows insertion of the housing into the shield, and after rotating the housing the shield is released, allowing it to retain its ordinary shape. This makes the small slits 22 encompass small knobs 25 on the outside of the housing 1 preventing it from rotating. The straightening of the shield prohibits the housing from being removed due to the position of the spikes 24 inside small channels 23 in the shield. The need to bend the shield in combination with the need to simultaneously rotate the housing in order to remove it makes this a safe and child proof locking mechanism. FIG. 11*b* is a detailed view of the locking mechanism. FIGS. 11*c-d* show how the device is rotated and locked in FIG. 11*c* vs unlocked in 11*d*.

Figure 12:
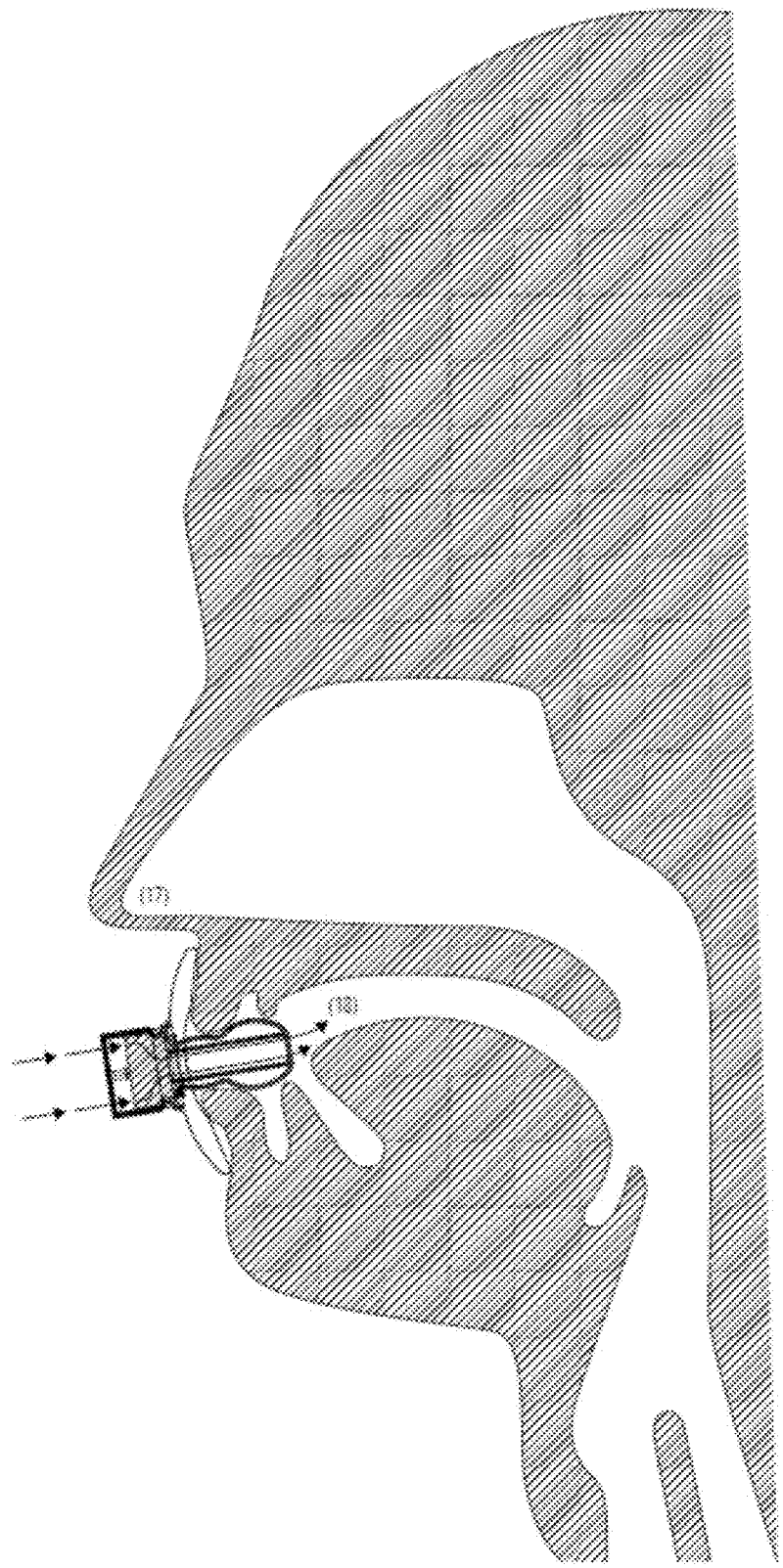
FIG. 12 pictures how the invention according to the embodiment as shown in FIG. 5a may divert airstreams in inhalation.
Figure 13:
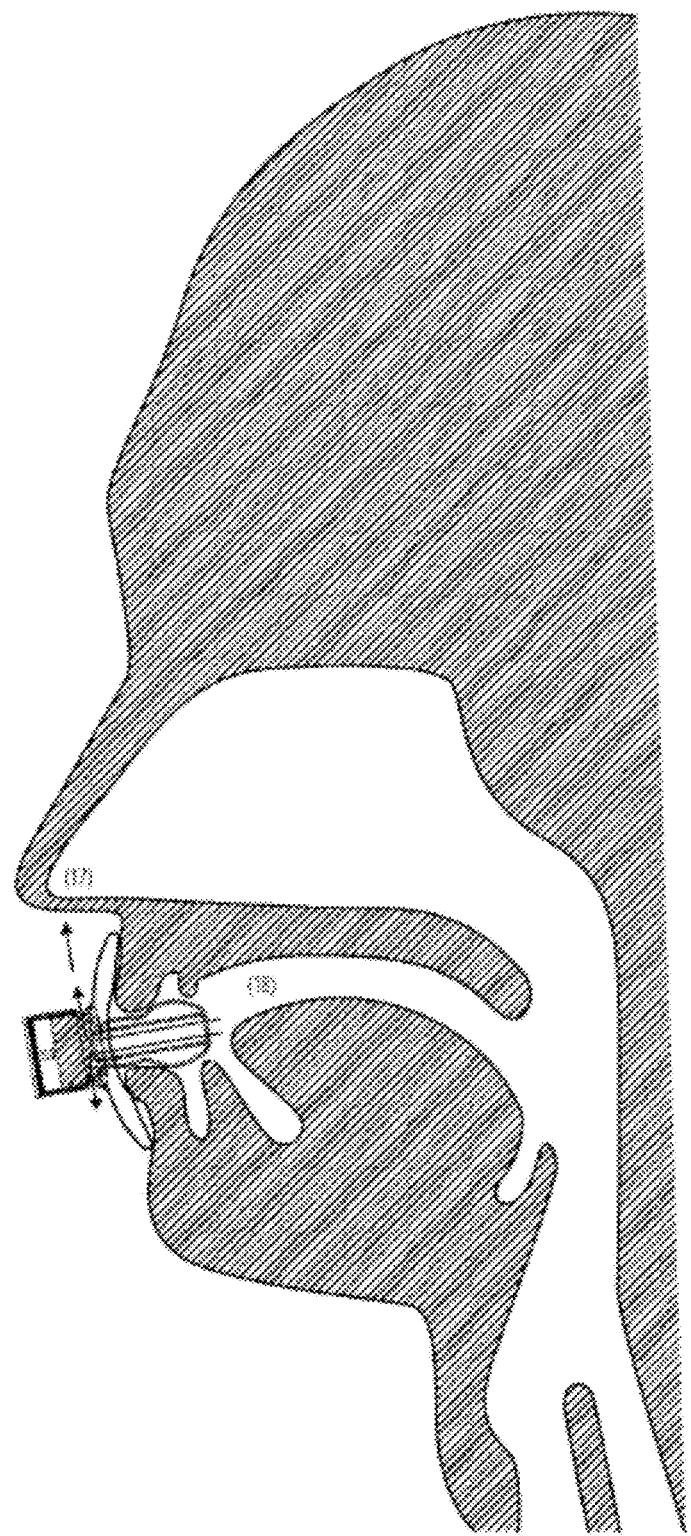
FIG. 13 pictures how the invention according to the embodiment as shown in FIG. 5a may divert airstreams in exhalation.

FIG. 12 pictures how the invention diverts airstreams in inhalation. FIG. 13 pictures how the invention diverts airstreams in exhalation. More specifically, in FIGS. 12 and 13, it is shown how the air flows through the device with arrows. As can be seen exhaled air (FIG. 13) can take one or several paths depending on the intentions of the manufacturer. Inhaled air passes through the filter device 2 and via the HME device 16 to the user's respiratory tract 17 and 18 enabling the creation of a conditioned microclimate around the respiratory orifices of the user. Exhaled air 20 is diverted from the housing 1 in order to avoid dampening of the filter device 2 and to take advantage of the conditioned air, flushing polluted external air with clean air from the lungs, thus diluting the outside air from toxic substances. This conditions the air around the respiratory orifices and contributes in the creation of a microclimate more suitable for breathing compared to the surrounding air.

As appears from these drawings, both inhalation and exhalation may be utilized to condition air in accordance with the invention, but neither excludes the other. In other words, the two functions may be operated independently of one another. Thus, thanks to these advantages and other, the invention enables to create a more suitable microclimate around the user's respiratory tract, obviating the need for any mechanical or other device inserted or otherwise manipulating the nose of the user. The advantage of this is a considerably more user friendly and comfortable device with an increased usability, especially in the case of infants.

The pacifier according to the invention is capable of conditioning inhaled as well as exhaled air. The invention may be a passive air conditioning device comprising HEM device and/or filter device. The device is capable of conditioning air around the orifices of the respiratory system of the individual. One advantage of the invention is that contrary to some prior art, it is driven solely by the respiration of the individual. In this context, it is understood that the term "individual" refers to a human user.

The term "conditioning" is used herein for a general improvement of the quality of breathing air. The term "breathe-through" pacifier means herein a pacifier through which the breathing of an individual is allowed. The term "mouth-breathing" means herein breathing that takes place through the mouth rather than through the nose of an individual.

The invention claimed is:

1. A pacifier comprising a reusable suction part and at least one exchangeable housing part which are releasably connectable to each other,
   wherein said suction part comprises a nipple and a shield connected to each other,
   wherein said suction part comprises a passageway through which a fluid can pass from outside the pacifier to inside a mouth of a user of the pacifier such that the pacifier is configured as a breath-through pacifier,
   wherein said suction part comprises at least one first connection device,
   wherein said housing part comprises a housing and at least one second connection device which is releasably connectable to the at least one first connection device,
   wherein said housing comprises at least one heat and moisture exchanger (HME) device and/or at least one filter device comprising a bacterial and/or particulate filter,
   wherein the housing, of said housing part, comprises an interior space which is defined by a lid, surrounding walls connected to the lid and a second connection interface which is provided opposite the lid, wherein said second connection interface is at least partly open into the interior space of the housing and is configured for mating with a first connection interface of the suction part, and
   wherein the lid comprises air openings through which air can pass and wherein the HME device and/or the filter device are provided within the interior space of the housing such that air passing between the air openings in the lid and the second connection interface of the housing also has to pass the HME device and/or the filter device.

2. A pacifier according to claim 1, wherein said passageway comprises a first end and a second end between which a fluid can pass, which first end is provided at a first connection interface of the suction part configured for mating with a second connection interface of the housing part and which second end of the passageway is provided in a part of the nipple which is configured to be positioned within a user's mouth during use of the pacifier, whereby a fluid can pass through the passageway between the first connection interface of the suction part and the inside of a user's mouth during use of the pacifier.

3. Pacifier according to claim 1, wherein the HME device and/or the filter device is secured within the interior space of the housing by at least one grating which is welded to the surrounding walls.

4. Pacifier according to claim 1, wherein the first or the second connection device comprises at least one recess and wherein the other one of the first or the second connection device comprises at least one protruding part whereby the at least one recess is configured to receive the at least one protruding part when the suction part and the housing part are connected.

5. Pacifier according to claim 4, wherein the one of the first or second connection device comprising at least one recess further comprises a channel and a locking edge which are configured for allowing rotation of the housing part in relation to the suction part and locking of the protruding part.

6. Pacifier according to claim 1, wherein the housing part further comprises a movable inner housing which is provided freely moving inside the housing and which in a first position will cover exhalation perforations provided in the housing and in a second position will not cover the exhalation perforations but instead cover inhalation openings provided in the housing.

7. Pacifier according to claim 6, wherein said exhalation perforations are positioned in a surrounding wall of the housing such that exhaled air is directed toward a nose of the user of the pacifier.

8. A replacement exchangeable housing part configured to be used in a pacifier according to claim 1, wherein said replacement housing part comprises a housing and at least one second connection device which is releasably connectable to the at least one first connection device of the suction part,
   wherein said housing comprises at least one heat and moisture exchanger (HME) device and/or at least one filter device comprising a bacterial and/or particulate filter,
   wherein the housing of the housing part comprises an interior space which is defined by a lid, surrounding walls connected to the lid and a second connection interface which is provided opposite the lid, wherein said second connection interface is at least partly open into the interior space of the housing and is configured for mating with the first connection interface of the suction part, and
   wherein the lid comprises air openings through which air can pass and wherein the HME device and/or the filter device are provided within the interior space of the housing such that air passing between the air openings in the lid and the second connection interface of the housing also has to pass the HME device and/or the filter device.

9. Replacement exchangeable housing part according to claim 8, wherein the HME device and/or the filter device is secured within the interior space of the housing by at least one grating which is welded to the surrounding walls.

10. Replacement exchangeable housing part according to claim 8, wherein the second connection device comprises at least one recess or at least one protruding part.

11. Replacement exchangeable housing part according to claim 8, wherein the housing part further comprises a movable inner housing which is provided freely moving inside the housing and which in a first position will cover exhalation perforations provided in the housing and in a second position will not cover the exhalation perforations but instead cover inhalation openings provided in the housing.

12. Replacement exchangeable housing part according to claim 11, wherein said exhalation perforations are positioned in a surrounding wall of the housing such that exhaled air is directed toward a nose of the user of the pacifier.

13. A pacifier system comprising a reusable suction part and at least two exchangeable housing parts according to claim 1.

* * * * *